United States Patent
Smith et al.

(10) Patent No.: US 7,939,501 B2
(45) Date of Patent: May 10, 2011

(54) OPHTHALMIC AND CONTACT LENS SOLUTIONS CONTAINING PEPTIDES AS PRESERVATIVE

(76) Inventors: Francis X. Smith, Salem, NH (US); Kathryn S. Crawford, Andover, MA (US)

(*) Notice: Subject to any disclaimer, the term of this patent is extended or adjusted under 35 U.S.C. 154(b) by 923 days.

(21) Appl. No.: 10/593,352

(22) PCT Filed: Apr. 15, 2004

(86) PCT No.: PCT/US2004/011575
§ 371 (c)(1), (2), (4) Date: Jun. 29, 2007

(87) PCT Pub. No.: WO2004/091438
PCT Pub. Date: Oct. 28, 2004

(65) Prior Publication Data
US 2008/0167246 A1 Jul. 10, 2008

Related U.S. Application Data

(60) Provisional application No. 60/462,940, filed on Apr. 15, 2003.

(51) Int. Cl.
*A61K 38/08* (2006.01)
*A61L 12/14* (2006.01)

(52) U.S. Cl. ....... 514/21.5; 424/427; 424/429; 514/839; 530/327

(58) Field of Classification Search .................. None
See application file for complete search history.

(56) References Cited

U.S. PATENT DOCUMENTS

| | | |
|---|---|---|
| 2,976,576 A | 3/1961 | Wiehterle et al. |
| 3,429,576 A | 2/1969 | Yoshiaki |
| 3,503,393 A | 3/1970 | Manley |
| 3,591,329 A | 7/1971 | Chromecek at al. |
| 3,689,673 A | 9/1972 | Phares, Jr, |
| 3,755,561 A | 8/1973 | Rankin |
| 3,873,696 A | 3/1975 | Randeri et al. |
| 3,876,768 A | 4/1975 | Blank |
| 3,888,782 A | 6/1975 | Boghosian et al. |
| 3,910,296 A | 10/1975 | Karageozian et al. |
| 3,911,107 A | 10/1975 | Krezanoski |
| 3,912,450 A | 10/1975 | Boucher |
| 3,943,251 A | 3/1976 | Medow et al. |
| 4,022,834 A | 5/1977 | Gundersen |
| 4,029,817 A | 6/1977 | Blanco et al. |
| 4,046,706 A | 9/1977 | Krezanoski |
| 4,136,173 A | 1/1979 | Pramoda et al. |
| 4,136,175 A | 1/1979 | Rideout et al. |
| 4,136,534 A | 1/1979 | Villa |
| 4,209,817 A | 6/1980 | McGinnis |
| 4,354,952 A | 10/1982 | Riedhammer et al. |
| 4,361,458 A | 11/1982 | Grajek et al. |
| 4,361,548 A | 11/1982 | Smith et al. |
| 4,361,549 A | 11/1982 | Kung et al. |
| 4,394,381 A | 7/1983 | Sherrill |
| 4,439,417 A | 3/1984 | Matsunaga et al. |
| 4,525,346 A | 6/1985 | Stark |
| 4,599,360 A | 7/1986 | Fukami et al. |
| RE32,672 E | 5/1988 | Huth et al. |
| 4,748,189 A | 5/1988 | Su et al. |
| 4,783,488 A | 11/1988 | Ogunbiyi et al. |
| 4,820,352 A | 4/1989 | Riedhammer et al. |
| 4,826,879 A | 5/1989 | Yamamoto et al. |
| 4,836,986 A | 6/1989 | Ogunbiyi et al. |
| 4,863,900 A | 9/1989 | Pollock et al. |
| 4,891,423 A | 1/1990 | Stockel |
| 4,894,454 A | 1/1990 | Paradies |
| 4,988,710 A | 1/1991 | Olney |
| 4,997,626 A | 3/1991 | Dziabo et al. |
| 5,030,721 A | 7/1991 | Kasai et al. |
| 5,078,908 A | 1/1992 | Ripley et al. |
| 5,089,261 A | 2/1992 | Nitecki et al. |
| 5,122,354 A | 6/1992 | Tsuji et al. |
| 5,174,872 A | 12/1992 | Scott |
| 5,175,161 A | 12/1992 | Yokoyama et al. |
| 5,182,258 A | 1/1993 | Chiou |
| 5,192,535 A | 3/1993 | Davis et al. |
| 5,279,673 A | 1/1994 | Dziabo et al. |
| 5,300,296 A | 4/1994 | Holly et al. |
| 5,306,440 A | 4/1994 | Ripley et al. |
| 5,361,287 A | 11/1994 | Williamson |
| 5,380,303 A | 1/1995 | Holly et al. |
| 5,439,572 A | 8/1995 | Pankow |
| 5,449,658 A | 9/1995 | Unhoch et al. |
| 5,494,937 A | 2/1996 | Asgharian et al. |

(Continued)

FOREIGN PATENT DOCUMENTS

EP 0 923 950 A3 12/2000
(Continued)

OTHER PUBLICATIONS

Sousa et al. The Use of Synthetic Cecropin (d5c) in Diinfecting Contact Lens Solutions CLAO Journal. vol. 22. No. 2, pp. 114-117. Apr. 1996.*
Schwab et al. "In vitro activities of designed antimicrobial peptides against multidrug-resistant cystic fibrosis pathogens." Antimicrobial Agents and Chemotherapy , 43(6), 1435-1440. 1999.*
Sajjan et al. "P-113D, an Antimicrobial Peptide Active against Pseudomonas aeruginosa, Retains Activity in the Presence of Sputum from Cystic Fibrosis Patients" Antimicrob. Agents Chemother. Dec. 2001 45: 3437-3444.*
Ballweber et al., "In Vitro Microbicical Activities of Cecropin Peptides D2A21 and D4E1 and Gel Formulations Containing 0.1 to 2% D2A21 against *Chlamydia trachomatis*",Antimicrobial Agents and Chemotheraphy, Jan. 2002, pp. 34-41, vol. 46, No. 1.

(Continued)

*Primary Examiner* — Anish Gupta
(74) *Attorney, Agent, or Firm* — Hiscock & Barclay, LLP

(57) ABSTRACT

A contact lens solution comprising 0.001 to 10 weight percent or a preservative enhancer chosen from the group consisting of: D4E1, D2A21, and P-113; and at least 0.0001 weight percent of a preservative, and where the concentration of chloride in said solution is less than 0.2 percent by weight.

17 Claims, No Drawings

U.S. PATENT DOCUMENTS

| | | |
|---|---|---|
| 5,547,990 A | 8/1996 | Hall et al. |
| 5,591,773 A | 1/1997 | Grunberger et al. |
| 5,607,681 A | 3/1997 | Galley et al. |
| 5,624,958 A | 4/1997 | Isaacs et al. |
| 5,660,862 A | 8/1997 | Park et al. |
| 5,661,130 A | 8/1997 | Meezan et al. |
| 5,674,450 A | 10/1997 | Lin et al. |
| 5,691,379 A | 11/1997 | Ulrich et al. |
| 5,718,895 A | 2/1998 | Asgharlan et al. |
| 5,719,110 A | 2/1998 | Cook |
| 5,741,817 A | 4/1998 | Chowhan et al. |
| 5,770,582 A | 6/1998 | von Borstel et al. |
| 5,780,450 A | 7/1998 | Shade |
| 5,807,585 A | 9/1998 | Martin et al. |
| 5,811,446 A | 9/1998 | Thomas |
| 5,854,303 A | 12/1998 | Powell et al. |
| 5,869,468 A | 2/1999 | Freeman |
| 5,888,950 A | 3/1999 | Potini et al. |
| 5,891,733 A | 4/1999 | Inoue |
| 5,925,317 A | 7/1999 | Rogalskyj et al. |
| 5,925,371 A | 7/1999 | Ishiwatari |
| 5,942,218 A | 8/1999 | Kirschner et al. |
| 5,945,446 A | 8/1999 | Laub |
| 5,952,320 A | 9/1999 | Davidsen et al. |
| 5,965,736 A | 10/1999 | Akhavan-Tafti |
| 6,008,195 A | 12/1999 | Selsted |
| 6,022,732 A | 2/2000 | Bakhit et al. |
| 6,056,920 A | 5/2000 | Lepre |
| 6,117,869 A | 9/2000 | Picard et al. |
| 6,121,327 A | 9/2000 | Tsuzuki et al. |
| 6,126,706 A | 10/2000 | Matsumoto et al. |
| 6,139,646 A | 10/2000 | Asgharian et al. |
| 6,153,563 A | 11/2000 | Smith et al. |
| 6,153,568 A | 11/2000 | McCanna et al. |
| 6,162,393 A | 12/2000 | De Bruiju et al. |
| 6,309,596 B1 | 10/2001 | Xia et al. |
| 6,309,658 B1 | 10/2001 | Xia et al. |
| 6,432,893 B1 | 8/2002 | Doi et al. |
| 6,617,291 B1 | 9/2003 | Smith |
| 6,624,203 B1 | 9/2003 | Smith |
| 2003/0190258 A1 | 10/2003 | Smith |
| 2005/0042198 A1 | 2/2005 | Smith et al. |

FOREIGN PATENT DOCUMENTS

| | | | |
|---|---|---|---|
| ER | 0 812 592 A1 | | 12/1997 |
| GB | 1398058 | | 3/1973 |
| JP | 58010517 A | | 1/1983 |
| JP | 10-108899 | | 4/1998 |
| JP | 2000016965 A | | 1/2000 |
| RU | 2127100 | | 3/1999 |
| WO | WO 91/01763 | | 2/1991 |
| WO | WO 92/04905 | | 4/1992 |
| WO | WO 92/11876 | | 7/1992 |
| WO | WO 92/21049 | | 11/1992 |
| WO | WO 94/00160 | | 1/1994 |
| WO | WO 95/00176 | | 1/1995 |
| WO | WO 96/06603 | | 3/1996 |
| WO | WO9625183 | * | 8/1996 |
| WO | WO 97/34834 | | 9/1997 |
| WO | WO 97/41215 | | 11/1997 |
| WO | WO 99/23887 | | 5/1999 |
| WO | WO 99/37295 | | 7/1999 |
| WO | WO 00/07634 | | 2/2000 |
| WO | WO 00/11514 | | 3/2000 |

OTHER PUBLICATIONS

Creighton, Thomas E., "Proteins Structures and Molecular Properties", W.H. Freeman & Co., New York, 1984, pp. 179-182.

De Lucca et al., "Fungicidal Properties, sterol binding, and proteolytic resistance of the synthetic peptide D4E1", Canadian Journmal of Microbiology, Jun. 1998, pp. 514-520, vol. 44, No. 6.

Keay, L., Moser, P.W. and Wildo, B.S.,"Proteases of the Genus Bacillus. II. Alkaline Proteases", Biotechnology & Bioengineering, Mar. 1970, pp. 213-249, vol. XII.

Keay, L, and Moser, P.W., "Differentiation of Alkaline Pretenses form Bacillus Species", BiocheBiochemical and Biophysical Research Comm, 1969, pp. 600-604, vol. 34, No. 5.

Schutte, L., et al., "The Substitution Reaction of Histidine and Some Other Imidazol Derivatives With iodine", Tetrahedon, Supp. No. 7, 1965, pp. 295-306.

* cited by examiner

SEQUENCE LISTING

<160> NUMBER OF SEQ ID NOS: 4

<210> SEQ ID NO 1
<211> LENGTH: 17
<212> TYPE: PRT
<213> ORGANISM: Artificial Sequence
<220> FEATURE:
<223> OTHER INFORMATION: Synthetic peptide with beta-pleated sheet structure.

<400> SEQUENCE: 1

Phe Lys Leu Arg Ala Lys Ile Lys Val Arg Leu Arg Ala Lys Ile Lys

```
                1               5              10              15
Leu

<210> SEQ ID NO 2
<211> LENGTH: 23
<212> TYPE: PRT
<213> ORGANISM: Artificial Sequence
<220> FEATURE:
<223> OTHER INFORMATION: Synthetic peptide with alpha-helical
      structure.

<400> SEQUENCE: 2

Phe Ala Lys Lys Phe Ala Lys Lys Phe Lys Lys Phe Ala Lys Lys Phe
 1               5                  10                  15

Ala Lys Phe Ala Phe Ala Phe
            20

<210> SEQ ID NO 3
<211> LENGTH: 12
<212> TYPE: PRT
<213> ORGANISM: Artificial Sequence
<220> FEATURE:
<223> OTHER INFORMATION: Internal fragment

<400> SEQUENCE: 3

Ala Lys Arg His His Gly Tyr Lys Arg Lys Phe His
 1               5                  10

<210> SEQ ID NO 4
<211> LENGTH: 12
<212> TYPE: PRT
<213> ORGANISM: Homo Sapiens

<400> SEQUENCE: 4

Ala Lys Arg His His Gly Tyr Lys Arg Lys Phe His
 1               5                  10
```

OPHTHALMIC AND CONTACT LENS SOLUTIONS CONTAINING PEPTIDES AS PRESERVATIVE

CROSS-REFERENCE TO RELATED APPLICATIONS

This application claims priority to and the benefit of PCT application number PCT/US04/011575, filed Apr. 15, 2004, and U.S. provisional patent application Ser. No. 60/462,940, filed Apr. 15, 2003, which are incorporated herein by reference in their entirety.

REFERENCE TO A SEQUENCE LISTING, A TABLE, OR A PROGRAM LISTING

This application refers to a "Sequence Listing" listed below, which is provided as a paper copy and a computer readable form labeled "Sequence listing.txt" (1,422 bytes, created on Oct. 18, 2007, 11:02:13 AM), which is incorporated herein by reference in its entirety.

FIELD OF THE INVENTION

The present invention relates to the field of ophthalmic solutions and their uses. In particular the invention relates to contact lens cleaning solutions, contact lens rinsing and storing solutions, solutions to deliver active pharmaceutical agents to the eye, solutions for disinfecting ophthalmic devices and the like.

BACKGROUND

The present invention relates to the field of ophthalmic solutions and especially to the aspects of preservative efficacy and comfort after prolonged use. These ophthalmic solutions have been used for some period of time and are available as over the counter products. Solutions that are used in direct contact with corneal tissue such as the delivery of active pharmaceutical agent to the eye, or indirectly, such as the cleaning, conditioning or storage of devices that will come in contact with corneal tissue, such as contact lenses, there is a need to insure that these solution do not introduce sources of bacterial or other microbial infection. Thus preservatives are included to reduce the viability of microbes in the solution and to lessen the chance of contamination of the solution by the user since many of the solutions are bought, opened, used, sealed and then reused.

State of the art preservative agents include polyhexamethylene biguanide (phmb), POLYQUAD™, chlorhexidine, and benzalkonium chloride, and the like, all of which at some concentration irritate corneal tissue and lead to user discomfort. Therefore, a solution that employs a given amount of a preservative agent, but which is made more effective by addition of an agent that is not a preservative agent would be desired.

SUMMARY OF THE INVENTION

The present invention relates to improved ophthalmic solutions that employ certain amphipathic peptides disclosed in U.S. Pat. Nos. 5,968,904; 6,001,805 and 6,191,110 in order to more effectively preserve solutions and to reduce the degree to which cationic preservatives will deposit on contact lenses. Ophthalmic solutions are here understood to include contact lens treatment solutions, such as cleaners, soaking solutions, conditioning solutions and lens storage solutions, as well as wetting solutions and in-eye solutions for treatment of eye conditions.

As used herein, the term "amphipathic" in application to a peptide or class of peptides means peptide(s) which contain hydrophilic and hydrophobic amino acid moieties (side chains) which are oriented in relation to one another so that the peptide(s) have discrete hydrophilic and hydrophobic faces or regions defined by a multiplicity of the respective hydrophilic and hydrophobic side chains. For example, when the peptide is in an amphipathic alpha-helix conformation, the hydrophobic amino acid side chains are oriented on one face of the alpha helix while the hydrophilic amino acid side chains are oriented on the other face of the alpha helix. When the peptide is amphipathic and exists (in solution) in a beta-pleated sheet conformation, the peptide likewise exhibits hydrophobic and hydrophilic faces deriving from the alignment of the oriented amino acid side chains of the molecule.

As used herein, the term "defensin-class peptide" means either a natural defensin peptide which is provided in isolated form as an active ingredient of the composition employed for wound healing treatment in accordance with U.S. Pat. No. 6,191,110, or else a synthetic peptide which is homologous to the natural defensin peptide, containing between 17 and 39 amino acids along its length, and forming amphipathic beta-pleated sheets in solution.

A wide variety of amphipathic peptides may be effectively utilized in the broad practice of the present invention, including, but not limited to, natural and synthetic melittin-class, cecropin-class, magainin-class, and defensin-class peptides. The beta pleated sheet conformation of peptides potentially usefully employed in the broad practice of the present invention may be readily determined by the circular dichroism technique described in Proteins, Creighton, Thomas E., W.H. Freeman & Co., New York (1984), pp. 179-182.

The solutions specifically described herein have 0.0001 to about 3 percent of the peptide in combination with other active ingredients useful in ophthalmic solutions such as buffers, preservatives, surfactants, and antimicrobial agents.

The preservatives that are specifically useful are cationic polymeric preservatives such as polyhexamethylene biguanide (phmb), POLYQUAD™, chlorhexidine, and benzalkonium chloride, as well as other cationic preservatives that may prove useful in the present invention as well. The cationic preservatives are used at effective amounts as preservatives, and in the instance of PHMB from 0.0001 percent by weight to higher levels of about 0.01 weight percent. Specifically, The cationic polymeric preservative includes polymeric biguanides such as polymeric hexamethylene biguanides (PHMB), and combinations thereof. such cationic polymeric biguanides, and water-soluble salts thereof, having the following formula:

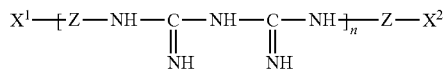

wherein Z is an organic divalent bridging group which may be the same or different throughout the polymer, n is on average at least 3, preferably on average 5 to 20, and $X^1$ and $X^2$ are

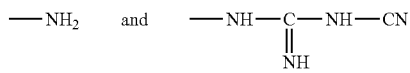

One preferred group of water-soluble polymeric biguanides will have number average molecular weights of at least 1,000 and more preferably will have number average molecular weights from 1,000 to 50,000. Suitable water-soluble salts of the free bases include, but are not limited to hydrochloride, borate, acetate, gluconate, sulfonate, tartrate and citrate salts.

The above-disclosed biguanides and methods of preparation are described in the literature. For example, U.S. Pat. No. 3,428,576 describes the preparation of polymeric biguanides from a diamine and salts thereof and a diamine salt of dicyanimide.

Most preferred are the polymeric hexamethylene biguanides, commercially available, for example, as the hydrochloride salt from Zeneca (Wilmington, Del.) under the trademark COSMOCIL™ CQ. Such polymers and water-soluble salts are referred to as polyhexamethylene (PHMB) or polyaminoptopyl biguanide (PAPB). The term polyhexamethylene biguanide, as used herein, is meant to encompass one or more biguanides having the following formula:

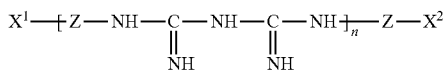

wherein Z, $X^1$ and $X^2$ are as defined above and n is from 1 to 500.

Depending on the manner in which the biguanides are prepared, the predominant compound falling within the above formula may have different $X^1$ and $X^2$ groups or the same groups, with lesser amounts of other compounds within the formula. Such compounds are known and are disclosed in U.S. Pat. No. 4,758,595 and British Patent 1,432,345, which patents are hereby incorporated. Preferably, the water-soluble salts are compounds where n has an average value of 2 to 15, most preferably 3 to 12.

It was found that an unexpected preservative efficacy was displayed when certain peptides were used in conjunction with the cationic preservative. Other preservatives may be used as well. The other components of the solution are used at levels known to those skilled in the art in order to improve the wearability of lenses and when used directly in the eye, to provide increased resistance to infection. These peptides used in ophthalmic solutions increase preservative efficacy in certain formulations, provide increased resistance to infection in corneal tissue, in certain formulations, and improve the quality of tears in certain formulations.

The formulations may also include buffers such as phosphates, bicarbonate, citrate, borate, ACES, BES, BICINE, BIS-Tris, BIS-Tris Propane, TRIS, HEPES, HEPPS, imidazole, MES, MOPS, PIPES, TAPS, TES, Glycine, and Tricine Surfactants that might be employed include polysorbate surfactants, polyoxyethylene surfactants, phosphonates, saponins and polyethoxylated castor oils, but preferably the polyethoxylated castor oils. These surfactants are commercially available. The polyethoxylated castor oils are sold by BASF under the trademark CREMAPHOR.

Inositol, mannitol, sorbitol, sucrose, dextrose, glycerin, propylene glycol and other simple saccharides and polysaccharides may be included in the solutions and are all commercially available, and well enough understood to be formulated into products within the scope of the invention by those skilled in the art.

The solutions of the present invention may contain other additives including but not limited to buffers, tonicity agents, demulcents, wetting agents, preservatives, sequestering agents (chelating agents), surface active agents, and enzymes.

Other aspects include adding to the solution from 0.001 to 1 weight percent chelating agent (preferably disodium EDTA) and/or additional microbicide, (preferably 0.00001 to 0.1 or 0.0000 1 to 0.01) weight percent polyhexamethylene biquanide (PHMBO, N-alkyl-2-pyrrolidone, chlorhexidine, polyquaternium-1, hexetidine, bronopol, alexidine, low concentrations of hydrogen peroxide, and ophthalmologically acceptable salts thereof.

Ophthalmologically acceptable chelating agents useful in the present invention include amino carboxylic acid compounds or water-soluble salts thereof, including ethylenediaminetetraacetic acid, nitrilotriacetic acid, diethylenetriamine pentaacetic acid, hydroxyethylethylenediaminetriacetic acid, 1,2-diaminocyclohexanetetraacetic acid, ethylene glycol bis (beta-aminoethyl ether) in N, N, N', N' tetraacetic acid (EGTA), aminodiacetic acid and hydroxyethylamino diacetic acid. These acids can be used in the form of their water soluble salts, particularly their alkali metal salts. Especially preferred chelating agents are the di-, tn- and tetra-sodium salts of ethylenediaminetetraacetic acid (EDTA), most preferably disodium EDTA (Disodium Edetate).

Other chelating agents such as citrates and polyphosphates can also be used in the present invention. The citrates which can be used in the present invention include citric acid and its mono-, di-, and tri-alkaline metal salts. The polyphosphates which can be used include pyrophosphates, triphosphates, tetraphosphates, trimetaphosphates, tetrametaphosphates, as well as more highly condensed phosphates in the form of the neutral or acidic alkali metal salts such as the sodium and potassium salts as well as the ammonium salt.

The pH of the solutions should be adjusted to be compatible with the eye and the contact lens, such as between 6.0 to 8.0, preferably between 6.8 to 7.8 or between 7.0 to 7.6. Significant deviations from neutral (pH 7.3) will cause changes in the physical parameters (i.e. diameter) in some contact lenses. Low pH (pH less than 5.5) can cause burning and stinging of the eyes, while very low or very high pH (less than 3.0 or greater than 10) can cause ocular damage.

The additional preservatives employed in the present invention are known, such as polyhexamethylene biguanide, N-alkyl-2-pyrrolidone, chlorhexidine, polyhexamethylenebiguanide, alexidine, polyquaternium-1, hexetidine, bronopol and a very low concentration of hydrogen peroxide, e.g., 30 to 200 ppm.

The solutions of the invention are compatible with both rigid gas permeable and hydrophilic contact lenses during storage, cleaning, wetting, soaking, rinsing and disinfection.

A typical aqueous solution of the present invention may contain additional ingredients which would not affect the basic and novel characteristics of the active ingredients described earlier, such as tonicity agents, surfactants and viscosity inducing agents, which may aid in either the lens cleaning or in providing lubrication to the eye. Suitable tonicity agents include sodium chloride, potassium chloride, glycerol or mixtures thereof. The tonicity of the solution is typically adjusted to approximately 240-310 milliosmoles per kilogram solution (mOsm/kg) to render the solution compatible with ocular tissue and with hydrophilic contact lenses. In one embodiment, the solution contains 0.01 to 0.2 weight percent sodium chloride. The important factor is to keep the concentrations of such additives to a degree no greater than that would supply a chloride concentration of no greater than about 0.2 mole percent.

Suitable viscosity inducing agents can include lecithin or the cellulose derivatives such as hydroxymethylcellulose, hydroxypropylcellulose and methylcellulose in amounts similar to those for surfactants, above.

Studies

Peptides were tested using a conventional Disinfection Efficacy antimicrobial assay (ISO 14729), commonly used in evaluating biocidal efficacy of preservatives for use in contact lens care solutions. Briefly, a known concentration of organisms are inoculated into the test solution, and allowed to incubate for a given amount of time, after which they are neutralized to inactivate the preservative. Samples are serially diluted and plated in duplicate onto petri plates onto which growth medium is poured. The plates are incubated at 35° C. (bacteria) or 25° C. (yeast and molds) for 48 hours. The average number of colony forming units is determined on countable plates (the dilution at which between 30 to 300 cfu/plate are observed, except when colonies are observed only on the −1 dilution plates). The log reduction resulting from exposure to the test solution is calculated based on the growth of positive controls plated simultaneously. Recovery controls, to confirm that the test solution is neutralized, and viability controls are also plated.

Experiment 1:

Purpose: SEQ ID NO. 3. P-113 was screened for anticandidal activity. Of the organism routinely used for preservative efficacy testing, *Candida albicans* is often the most resistant.

Method: *Candida albicans* (ATCC 10231) stock cultures were incubated and prepared to result in cell suspensions containing between $10^7$ and $10^8$ cfu/mL. The Disinfection Efficacy test, as described above, was used, with the following modification: Since the standard Dey-Engley broth used to neutralize preservatives was not necessarily expected to neutralize the peptide, 0.1% sodium laurel sulfate (SLS) was added to the neutralization solution. Controls confirmed that this was effective in neutralizing the peptide test solution. The peptide Was tested at a 100 μg/mL concentration in water with a 2 hour exposure time, which resulted in a 2.5 log reduction in Candida.

Conclusion: In our system, as in the studies performed by Demegen and others, SEQ ID NO. 3, P-113 is effective at killing *Candida albicans*.

Experiment 2

Purpose: To determine whether 4 distinct peptides, SEQ ID NO. 3 (P-113), SEQ ID NO. 4 (P-113D), SEQ ID NO. 1 (D4E1), and SEQ ID NO. 2 (D2A21) are effective in killing a variety of microorganisms Method: The Disinfection Efficacy test was used with the following organisms: *Staphylococcus aureus* (ATCC 6538), *Pseudomonas aeruginosa* (ATCC 9027), *Serratia marcesens* (ATCC 13880), *Candida albicans* (ATCC 10231), and *Fusarium solani* (ATCC 36031). The peptides were diluted in water at a concentration of 100 ug/mL (adjusted for purity). Organism cultures were prepared to result in an inoculum concentration between $10^7$ and $10^8$ cfu/mL. The test solutions were inoculated for a 1 hour and a 3 hour exposure period, neutralized with DEB with 0.1% SLS added, and plated in duplicate.

Results: One hour of peptide exposure at this concentration resulted in a dramatic biocidal effect, particularly for SEQ ID NO. 1 and SEQ ID NO. 2. The three hour exposure time resulted in a similar, or slightly but not significantly greater effect. The results from the 1 hour exposure time are shown in the Table below. SEQ ID NO. 3 and SEQ ID NO. 4 at this concentration was effective only on *P. aeruginosa, C. albicans,* and *F. solani*, but had no effect on either *S. aureus* and *S. marcescens*. A one hour exposure to both of the other two peptides resulted in complete kill of all 5 organisms.

| Test Microorganism | Solution ID | dilution | cfu | average cfu/mL | | Average Log Reduction |
|---|---|---|---|---|---|---|
| S. aureus | Positive Controls | −4 | 47 | 4.70E+05 | | |
| (ATCC 6538) | P113 | −4 | 61 | 6.10E+05 | | −0.11 |
| | P113D | −4 | 47 | 4.70E+05 | | 0.00 |
| | D4E1 | −1 | 0 | 0.00E+00 | > | 4.67 |
| | D2A21 | −1 | 0 | 0.00E+00 | > | 4.67 |
| P. aeruginosa | Positive Controls | −4 | 50 | 5.00E+05 | | |
| (ATCC 9027) | P113 | −1 | 6 | 6.00E+01 | | 3.92 |
| | P113D | −1 | 2 | 2.00E+01 | | 4.40 |
| | D4E1 | −1 | 0 | 0.00E+00 | > | 4.70 |
| | D2A21 | −1 | 0 | 0.00E+00 | > | 4.70 |
| S. marcescens | Positive Controls | −4 | 60 | 6.00E+05 | | |
| (ATCC 13880) | P113 | −4 | 40 | 4.00E+05 | | 0.18 |
| | P113D | −4 | 28 | 2.80E+05 | | 0.33 |
| | D4E1 | −1 | 0 | 0.00E+00 | > | 4.78 |
| | D2A21 | −1 | 0 | 0.00E+00 | > | 4.78 |
| C. albicans | Positive Controls | −4 | 86 | 8.60E+05 | | |
| (ATCC 10231) | P113 | −1 | 551 | 5.51E+03 | | 2.19 |
| | P113D | −2 | 33 | 3.30E+03 | | 2.42 |
| | D4E1 | −1 | 0 | 0.00E+00 | > | 4.93 |
| | D2A21 | −1 | 0 | 0.00E+00 | > | 4.93 |
| F. solani | Positive Controls | −4 | 16 | 1.60E+05 | | |
| (ATCC 36031) | P113 | −2 | 60 | 6.00E+03 | | 1.43 |
| | P113D | −2 | 64 | 6.40E+03 | | 1.40 |
| | D4E1 | −1 | 0 | 0.00E+00 | > | 4.20 |
| | D2A21 | −1 | 0 | 0.00E+00 | > | 4.20 |

Note:
Neutralizer controls for all solutions passed specifications with all organisms indicating the the test results are valid.

Conclusion. The selectivity of SEQ ID NO. 3 on *Candida* and *Pseudomonas* may prove useful for certain applications. There was no significant difference between the SEQ ID NO. 3 (L) and SEQ ID NO. 4. The broad spectrum efficacy of SEQ ID NO. 1 and SEQ ID NO. 2 indicates that these peptides may prove extremely useful for treating a wide variety of ocular infections, and in particular, contact-lens associated keratitis.

Experiment 3

Purpose: To establish a dose-response curve for SEQ ID NO. 3, SEQ ID NO. 1, and SEQ ID NO. 2, focusing specifically on their effectiveness against bacteria.

Method: The Disinfection Efficacy test was used as in experiment 2 using *Staphylococcus aureus* and *Pseudomonas aeruginosa*. The peptides were diluted in water at concentrations of 100, 33.3, 10, 3.33, and 1 ug/mL. The test solutions were inoculated for 1 hour, neutralized, and plated in duplicate.

Results: Complete kill of *P. aeruginosa* resulted from concentrations as low as 1 was not effective against *S. aureus*. Since the traditional logarhythamic response was not observed for most of these concentration series, the results are shown in tabular form below.

| Test Microorganism | Solution ID | Conc. (µg/mL) | dilution | cfu (average) | average cfu/mL | | Average Log Reduction |
|---|---|---|---|---|---|---|---|
| *S. aureus* ATCC 6538 T = 1 hr | Positive Control | | −4 | 36 | 3.60E+05 | | |
| | D4E1 | 100 | −1 | 0 | 0.00E+00 | > | 4.86 |
| | | 33 | −1 | 0 | 0.00E+00 | > | 4.86 |
| | | 10 | −1 | 0 | 0.00E+00 | > | 4.86 |
| | | 3.33 | −1 | 0 | 0.00E+00 | > | 4.86 |
| | | 1 | −1 | 1 | 5.00E+00 | | 4.86 |
| | D2A21 | 100 | −1 | 0 | 0.00E+00 | > | 4.86 |
| | | 33 | −1 | 0 | 0.00E+00 | > | 4.86 |
| | | 10 | −1 | 1 | 1.00E+01 | | 4.56 |
| | | 3.33 | −1 | 0 | 0.00E+00 | > | 4.86 |
| | | 1 | −1 | 112 | 1.12E+03 | | 2.51 |
| | P-113 | 100 | −4 | 38 | 3.80E+05 | | −0.02 |
| | | 33 | −4 | 34 | 3.40E+05 | | 0.03 |
| | | 10 | −3 | 202 | 2.02E+05 | | 0.25 |
| | | 3.33 | −3 | 144 | 1.44E+05 | | 0.40 |
| | | 1 | −3 | 60 | 5.95E+04 | | 0.78 |
| *P. aeruginosa* ATCC 9027 T = 1 hr | Positive Controls | initial | −4 | 53.5 | 5.35E+05 | | |
| | D4E1 | 100 | −1 | 0 | 0.00E+00 | > | 5.03 |
| | | 33 | −1 | 1 | 5.00E+00 | | 5.03 |
| | | 10 | −1 | 0 | 0.00E+00 | > | 5.03 |
| | | 3.33 | −1 | 0 | 0.00E+00 | > | 5.03 |
| | | 1 | −1 | 1 | 1.00E+01 | | 4.73 |
| | D2A21 | 100 | −1 | 0 | 0.00E+00 | > | 5.03 |
| | | 33 | −1 | 0 | 0.00E+00 | > | 5.03 |
| | | 10 | −1 | 0 | 0.00E+00 | > | 5.03 |
| | | 3.33 | −1 | 0 | 0.00E+00 | > | 5.03 |
| | | 1 | −1 | 0 | 0.00E+00 | > | 5.03 |
| | P-113 | 100 | −1 | 0 | 0.00E+00 | > | 5.03 |
| | | 33 | −1 | 0 | 0.00E+00 | > | 5.03 |
| | | 10 | −1 | 2 | 1.50E+01 | | 4.55 |
| | | 3.33 | −1 | 1 | 5.00E+00 | | 5.03 |
| | | 1 | −1 | 39 | 3.90E+02 | | 3.14 |

Note:
Neutralizer controls for all solutions passed specifications with all organisms indicating the the test results are valid.

Conclusion: Peptides SEQ ID NO. 1 and SEQ ID NO. 2 are extremely effective against the two bacterial species tested, indicating that both gram-positive and gram-negative bacteria might be suitable targets for therapeutic applications of these molecules. The low concentrations required for complete kill of 105 cfu/mL bacteria indicate that the therapeutic index (safety) might be very high, since concentrations of peptide as high as XXX/mL have been reported to be nontoxic in XXX cells.

What is claimed is:

1. An ophthalmic solution comprising 0.001 to 10 weight percent of SEQ ID NO. 3; and at least 0.0001 weight percent of a preservative agent, and where the concentration of chloride in said solution not more than 0.2 percent by weight.

2. The solution of claim 1, wherein said preservative agent is a cationic polymeric preservative having a concentration between 1 and 100 parts per million.

3. The solution of claim 1, further comprising a physiologically compatible buffer selected from the group consisting of phosphate, bicarbonate, citrate, borate, ACES, BES, BICINE, BIS, BIS-Tris, BIS-Tris Propane, HEPES, HEPPS, imidazole, Tris, MES, MOPS, PIPES, TAPS, TES, Glycine and Tricine.

4. The solution of claim 1, further comprising between 0.01% and 5.0% glycerin.

5. The solution of claim 1 further comprising between 0.01% and 2.0% of decanedioic acid.

6. The solution of claim 1 further comprising a wetting agent selected from the group consisting of polysorbate surfactants, polyoxyethylene surfactants, phosphonates, saponins and polyethoxylated castor oils.

7. The solution of claim 1 further comprising a sequestering agent selected from the group consisting as ethylenediaminetetraacetic acid, phosphonates, citrate, gluconate and tartarate.

8. The solution of claim 1, wherein the concentration of chloride in said solution not more than 0.2 mole percent.

9. The solution of claim 1, wherein said solution has a pH between 6.0 and 8.0.

10. A method for wetting a contact lens comprising the steps of:
providing a contact lens; and
contacting said contact lens with a solution comprising 0.001 to 10 weight percent of SEQ ID NO. 3; and at least 0.0001 weight percent of a preservative agent, and where the concentration of chloride in said solution not more than 0.2 percent by weight.

11. The method of claim 10, wherein said preservative agent is a cationic polymeric preservative having a concentration between 1 and 100 parts per million.

12. The method of claim 11, wherein said cationic polymeric preservative is polyhexamethylene biguanide.

13. The method of claim 10, wherein said solution further comprises a physiologically compatible buffer selected from the group consisting of phosphate, bicarbonate, citrate, borate, ACES, BES, BICINE, BIS, BIS-Tris, BIS-Tris Propane, HEPES, HEPPS, imidazole, Tris, MES, MOPS, PIPES, TAPS, TES, Glycine and Tricine.

14. A method for delivering an ophthalmic solution to the eye comprising the steps of:
providing a bottle comprising a solution comprising 0.001 to 10 weight percent of SEQ ID NO. 3; and at least 0.0001 weight percent of a preservative agent, and where the concentration of chloride in said solution not more than 0.2 percent by weight; and delivering said solution form said bottle to an eye such that the solution comes in direct contact with corneal tissue.

15. The method of claim 14, wherein said preservative agent is a cationic polymeric preservative having a concentration between 1 and 100 parts per million.

16. The method of claim 15, wherein said cationic polymeric preservative is polyhexamethylene biguanide.

17. The method of claim 14, wherein said solution further comprises a physiologically compatible buffer selected from the group consisting of phosphate, bicarbonate, citrate, borate, ACES, BES, BICINE, BIS, BIS-Tris, BIS-Tris Propane, HEPES, HEPPS, imidazole, Tris, MES, MOPS, PIPES, TAPS, TES, Glycine and Tricine.

* * * * *